United States Patent [19]

Wätjen et al.

[11] Patent Number: 5,223,527
[45] Date of Patent: Jun. 29, 1993

[54] ISATINEOXIME DERIVATIVES AND THEIR USE

[75] Inventors: Frank Wätjen, Herlev; Jorgen Drejer, Vaerlose; Leif H. Jensen, Copenhagen, all of Denmark

[73] Assignee: NeuroSearch A/S, Glostrup, Denmark

[21] Appl. No.: 899,620

[22] Filed: Jun. 16, 1992

Related U.S. Application Data

[63] Continuation-in-part of Ser. No. 727,479, Jul. 9, 1991, abandoned.

[51] Int. Cl.[5] ............... A61K 31/445; A61K 31/40; C07D 401/12; C07D 209/62
[52] U.S. Cl. .................... 514/411; 514/323; 546/200; 548/450
[58] Field of Search .......... 548/450; 546/200; 514/323, 411

[56] References Cited

U.S. PATENT DOCUMENTS 5,155,110 10/1992 Connor et al. .............. 548/483

FOREIGN PATENT DOCUMENTS 432648 6/1991 European Pat. Off. .

OTHER PUBLICATIONS

Divis, Chemical Abstracts 73(2), Abstract 10333 (1970).
March, Advanced Organic Chemistry, pp. 805–806, John Wiley & Sons 1985.

Primary Examiner—Mary C. Lee
Assistant Examiner—Mary Susan H. Gabilan
Attorney, Agent, or Firm—Gordon W. Hueschen

[57]  ABSTRACT

A compound having the formula

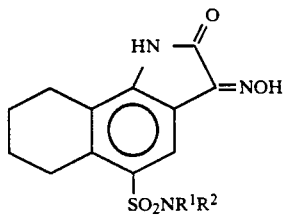

wherein
R[1] is $C_{1-6}$-alkyl which may be branched or cyclic;
R[2] is $C_{1-6}$-alkyl which may be branched or cyclic; or wherein R[1] and R[2] together represent $-(CH_2)_n-$, wherein n is 3, 4, 5.

and a method of treating disorders of a mammal, including a human, responsive to the blockade of glutamic and aspartic acid receptors, with the same.

6 Claims, No Drawings

ISATINEOXIME DERIVATIVES AND THEIR USE

This application is a continuation-in-part of our prior-filed copending application Ser. No. 727,479, filed Jul. 9, 1991, now abandoned.

The present invention relates to novel ring fused indole-2,3-dione oxime derivatives, a method of treatment therewith, pharmaceutical compositions comprising the compounds and to a method of preparing the novel compounds of the invention.

OBJECT OF THE INVENTION

It is an object of the present invention to provide novel isatine compounds which are useful in the treatment of diseases in mammals, including a human, and especially in the treatment of diseases which can be treated by antagonizing an excitatory amino acid of such mammal.

Another object of the present invention is to provide a method of treating diseases in mammals, including a human, responsive to the blockade of glutamic and aspartic acid receptors which comprises administering to a mammal in need thereof a compound of the invention.

A third object of the present invention is to provide novel pharmaceutical compositions for the treatment of diseases in mammals, including a human, responsive to the blockade of glutamic and aspartic acid receptors.

BACKGROUND OF THE INVENTION

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA), the $\mu$-amino-3-hydroxy-5-methyl-4-isoxazole propionic acid (AMPA) receptor, and the kainate receptor. This excitotoxic action is responsible for the loss os neurons in cerebrovascular disorders such as cerebral ischemia or cerebral infarction resulting from a range of conditions, such as thromboembolic or haemorrhagic stroke, cerebral vasospasm, hypoglycaemia, cardiac arrest, status epilepticus, perinatal asphyxia, anoxia such as from drowning, pulmonary surgery and cerebral trauma as well as lathyrism, Alzheimer's, Parkinsonism, and Huntington's diseases.

The compounds of the present invention may also be useful in the treatment of schizophrenia, epilepsy, anxiety, pain and drug addiction.

EPA 432648, published Jun. 19, 1991, discloses certain isatineoxime derivatives. Some of the compounds of the present invention are comprised by the generic disclosure of that European Patent Application. However, no compounds having the very important features and substituents as the compounds of the present invention are specifically disclosed in EPA 432648 although some of the compounds of the present invention are disclosed in a broad and generic way therein.

SUMMARY OF THE INVENTION

The invention then, inter alia, comprises the following, alone or in combination: A compound having the formula

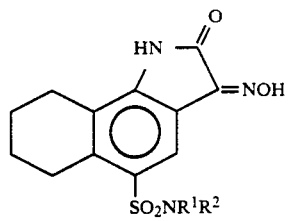

wherein
$R^1$ is $C_{1-6}$-alkyl which may be branched or cyclic;
$R^2$ is $C_{1-6}$-alkyl which may be branched or cyclic;
or wherein $R^1$ and $R^2$ together represent —$(CH_2)_n$—, wherein n is 3, 4, 5, .
and a compound as above which is 5-N,N-dimethylsulfamoyl-1H-6,7,8,9-tetrahydrobenz[g]indole-2,3-dione-3-oxime,
and a compound as above which is 5-(1-pyrolidinylsulfonyl)-1H-6,7,8,9-tetrahydrobenz[g]indole-2,3-dione-3-oxime,
and a method of treating disorders of a mammal, including a human, responsive to the blockade of glutamic and aspartic acid receptors, which comprises administering to a patient in need thereof a compound as first above in unit dosage form,
and a method as above wherein cerebrovascular disorders, Parkinsonism, anoxia, schizophrenia, migraine, epilepsy, pain, drug addiction, Alzheimer's disease and Huntington's disease are treated,
and further a pharmaceutical composition comprising a therapeutically-effective amount of a compound as first above together with a pharmaceutically-acceptable carrier,
and the use of a compound as first above for the preparation of a medicament useful in the treatment of disorders of a mammal, including a human, responsive to the blockade of glutamic or aspartic acid receptors,
and the use of a compound as first above for the preparation of a medicament useful in the treatment of cerebrovascular disorders, Parkinsonism, anoxia, anxiety, schizophrenia, migraine, epilepsy, pain, drug addiction, Alzheimer's disease and Huntington's disease, and the use as above wherein the compound is 5-N,N-dimethylsulfamoyl-1H-6,7,8,9-tetrahydrobenz[g]indole-2,3-dione-3-oxime.

Biological Activity

The compounds of the invention exhibit valuable biological properties because of their strong excitatory amino acid (EAA) antagonizing properties at the AMPA ((RS)-$\mu$-amino-3-hydroxy-5-methyl-4-isoxazolepropionic acid) binding site.

Further as compared to known glutamate antagonists acting at the same binding site (see for example EPA 283959) the compounds of the invention are extremely superior because of their high bioavailability.

The compound 5-N,N-dimethylsulfamoyl-1H-6,7,8,9-tetrahydrobenz[g]indole-2,3-dione-3-oxime for example exhibit an $IC_{50}$ of 2 $\mu$M in the AMPA binding assay as described by T. Honoré et al., Neuroscience Letters 54. 27–32 (1985).

The compound 5-N,N-dimethylsulfamoyl-1H-6,7,8,9-tetrahydrobenz[g]indole-2,3-dione-3-oxime has an $ED_{50}$ of 3 mg/kg when administered i.v. and of 30 mg/kg when administered orally in the AMPA seizure test as described below.

AMPA-Induced Clonic Seizures

AMPA given icv (intracerebroventricular) (15 μg/kg) NMRI to mice induces clonic seizures which should be inhibited by non-NMDA receptor antagonists.

Method

Test compound was given i.v. 5 min (or p.o. 30 min) before a 0.3 μg icv administration of AMPA to 10 female NMRI mice (weighing 24–26 g) per dose. The number of mice experiencing clonic seizures within the next 5 min was noted. An $ED_{50}$ value was calculated as the dose inhibiting 50% of the mice from having clonic seizures.

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredients or, more broadly, 0.1 to one hundred (100) milligrams, per tablet, are accordingly suitable representative unit dosage forms.

Solid forms of pharmaceutical compositions for p.o. administration and injectable solutions are preferred.

Method of Treating

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino acid dependent psychosis, excitatory amino acid dependent anoxia, excitatory amino acid dependent ischemia, excitatory amino acid dependent convulsions and excitatory amino acid dependent migraine. Suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLE 1 a)

5-chlorosulfonyl-1H-6,7,8,9-tetrahydrobenz[g]indole-2,3-dione 4 g (19.90 mmol) of 1H-6,7,8,9-tetrahydrobenz[g]indole-2,3-dione (prepared as in EPA-432648) is added portionwise to 15 ml chlorosulphonic acid while the temperature is kept at room temperature. The mixture is stirred for 30 minutes and is thereafter poured unto ice water. The precipitate is isolated and dried and is thereafter washed with diethylether/light petroleum and the precipitate is isolated.

b)

5-N,N-dimethylsulfamoyl-1H-6,7,8,9-tetrahydrobenz[g]-indole-2,3-dione 1 g (3.34 mmol) 5-chlorosulfonyl-1H-6,7,8,9-tetrahydrobenz[g]indole-2,3-dione is suspended in tetrahydrofuran (THF) (25 ml). The mixture is cooled on an ice bath and is exposed to gaseous dimethylamine for 5 minutes. The reaction mixture is evaporated and the residue is washed with ethylacetate/water. The precipitate is isolated by filtration and washed with THF. The crude product is purified by treatment with methylene chloride and ethylacetate. The resulting filtered solution is concentrated in vacuo and the precipitate is isolated and is washed with ethylacetate. Yield 0.24 g, M.p. 162°–165° C.

In exactly the same manner the following compound are prepared from pyrrolidine, piperidine, diethylamine and di-(n-butyl)amine.

5-(1-pyrrolidinyl-sulfonyl)-1H-6,7,8,9-tetrahydrobenz[g]indole-2,3-dione (isolated as an oil), 5-N,N-diethylsulfamoyl-1H-6,7,8,9-tetrahydrobenz[g]indole-2,3-dione (isolated as an oil), 5-(N,N-di-(n-butyl)sulfamoyl-1H-6,7,8,9-tetrahydrobenz[g]indole-2,3-dione (isolated as an oil), 5-(1-piperidyl-sulfonyl)-1H-6,7,8,9-tetrahydrobenz[g]indole-2,3-dione (isolated as an oil).

c)

5-N,N-dimethylsulfamoyl-1H-6,7,8,9-tetrahydrobenz[g]-indole-2,3-dione-3-oxime 0.2 g (0.65 mmol) of 5-N,N-dimethylsulfamoyl-1H-6,7,8,9-tetrahydrobenz[g]indole-2,3-dione is mixed with 0.05 g (0.71 mmol) hydroxylamine hydrochloride, 0.07 g (0.71 mmol) disodium carbonate and 7 ml of methanol and the mixture is stirred for 2 hours at room temperature. 5 ml water and acetic acid (few drops) is added and the resulting precipitate is isolated. Yield 0.16 g, M.p. 268°–270° C.

In exactly the same manner the following compound are prepared:

5-(1-pyrrolidinyl-sulfonyl)-1H-6,7,8,9-tetrahydrobenz[g]indole-2,3-dione-3-oxime, M.p. Brown oil, 5-(1-piperidyl-sulfonyl-1H-6,7,8,9-tetrahydrobenz[g]indole-2,3-dione-3-oxime, M.p. 256°–259° C., 5-N,N-di-(n-butyl)sulfamoyl-1H-6,7,8,9-tetrahydrobenz[g]indole-2,3-dione-3-oxime, M.p. 238°–240° C., 5-N,N-diethylsulfamoyl-1H-6,7,8,9-tetrahydrobenz[g]indole-2,3-dione-3-oxime, M.p. 244°–245° C.

We claim:

1. A compound having the formula

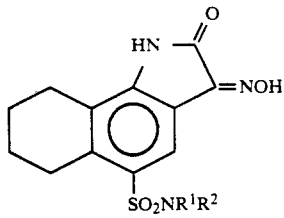

wherein $R^1$ is $C_{1-6}$-alkyl which may be branched or cyclic;

$R^2$ is $C_{1-6}$-alkyl which may be branched or cyclic; or wherein $R^1$ and $R^2$ together represent —$(CH_2)_n$—, wherein n is 3, 4, 5.

2. A compound of claim 1 which is 5-N,N-dimethylsulfamoyl-1H-6,7,8,9-tetrahydrobenz[g]-indole-2,3-dione-3-oxime.

3. A compound of claim 1 which is 5-(1-pyrrolidinylsulfonyl)-1H-6,7,8,9-tetrahydrobenz[g]-indole-2,3-dione-3-oxime.

4. A pharmaceutical composition useful for blockade of glutamic and aspartic acid receptors comprising an amount of a compound of claim 1 effective for such purpose with a pharmaceutically-acceptable carrier.

5. A method of treating disorders of a mammal, a responsive to the blockade of glutamic and aspartic acid receptors, which comprises administering to a patient in need thereof an amount of a compound of claim 1 which is effective for such purpose in unit dosage form.

6. The method of claim 5 wherein cerebrovascular disorders, Parkinsonism, anoxia, anxiety, epilepsy, schizophrenia, migraine, pain, drug addiction, Alzheimer's disease, or Huntingdon's disease, are treated.

* * * * *

UNITED STATES PATENT AND TRADEMARK OFFICE
CERTIFICATE OF CORRECTION

PATENT NO. : 5,223,527
DATED : June 29, 1993
INVENTOR(S) : Frank Wätjen, Jorgen Drejer, Leif H. Jensen It is certified that error appears in the above-indentified patent and that said Letters Patent is hereby corrected as shown below:

Column 1, line 39; "µ-amino- " should read -- α-amino- --.
Column 1, line 42; "os" should read -- of --.
Column 2, approximately line 18; move the opening bracket "[" from the end of line 18 to the beginning of line 19 and insert before "g", leaving the dash at the end of line 18.
Column 2, line 53; "((RS)-µ-amino-" should read -- ((RS)-α- amino- --.
Column 4, line 30; move the opening bracket "[" from the end of line 30 to the beginning of line 31 and insert before "g", leaving the dash at the end of line 30.
Column 4, line 54; "compound" should read -- compounds --.
Column 6, line 9; "purpose with" should read -- -- purpose together with --. (P. 9, Claim 4, line 2)
Column 6, line 10; delete "a" at the end of the line. (R&A 11-17-92, P. 1)
Column 6, line 18; "Huntingdon's" should read --Huntington's--.

Signed and Sealed this

Third Day of May, 1994

Attest:

BRUCE LEHMAN

Attesting Officer

Commissioner of Patents and Trademarks